United States Patent [19]
Pedros

[11] Patent Number: 6,096,074
[45] Date of Patent: Aug. 1, 2000

[54] STAPLING APPARATUS AND METHOD FOR HEART VALVE REPLACEMENT

[75] Inventor: Roberto Pedros, Seymour, Conn.

[73] Assignee: United States Surgical, Norwalk, Conn.

[21] Appl. No.: 09/013,836

[22] Filed: Jan. 27, 1998

[51] Int. Cl.[7] ........................................................ A61F 2/24
[52] U.S. Cl. ................................................................ 623/2
[58] Field of Search ........................................ 623/2, 900

[56] References Cited

U.S. PATENT DOCUMENTS

| | | |
|---|---|---|
| Re. 34,150 | 12/1992 | Santilli et al. . |
| 2,682,057 | 6/1954 | Lord . |
| 3,143,742 | 8/1964 | Cromie . |
| 3,371,352 | 3/1968 | Siposs et al. . |
| 3,464,065 | 9/1969 | Cromie . |
| 3,508,281 | 4/1970 | Cromie . |
| 3,524,202 | 8/1970 | Cromie . |
| 3,546,710 | 12/1970 | Shumakov et al. . |
| 3,574,865 | 4/1971 | Hamaker . |

(List continued on next page.)

FOREIGN PATENT DOCUMENTS

| | | |
|---|---|---|
| 809965 | 4/1969 | Canada . |
| 0103546 | 3/1984 | European Pat. Off. . |
| 0200419 | 11/1986 | European Pat. Off. . |
| 2033116 C1 | 4/1995 | Russian Federation .................... 623/2 |
| 207339 | 12/1967 | U.S.S.R. . |
| 782808 | 11/1980 | U.S.S.R. . |
| 878285 | 11/1981 | U.S.S.R. . |
| 969265 | 10/1982 | U.S.S.R. . |
| 1008937 | 7/1984 | U.S.S.R. . |
| 1507368 | 9/1989 | U.S.S.R. . |
| 1621912 | 1/1991 | U.S.S.R. . |
| 1690738 | 11/1991 | U.S.S.R. . |
| 1697790 | 12/1991 | U.S.S.R. . |
| WO 87/05489 | 9/1987 | WIPO . |
| WO 91/01697 | 2/1991 | WIPO . |
| WO 91/17720 | 11/1991 | WIPO . |
| WO 93/01768 | 2/1993 | WIPO . |
| WO 94/01062 | 1/1994 | WIPO . |
| WO 94/18909 | 9/1994 | WIPO . |

OTHER PUBLICATIONS

The Journal of Thoracic and Cardiovascular Surgery, vol. 52, No. 4, Oct. 1966, p. 41.
The Journal of Thoracic and Cardiovascular Surgery, George J. Magovern, M.D. et al., vol. 48, No. 3, Sep. 1964, pp. 346–361.
The Journal of Thoracic And Cardiovascular Surgery, G.J. Magovern, M.D. et al., vol. 46, Dec. 1963, No. 6, pp. 726–736.
The Journal of Thoracic And Cardiovascular Surgery, vol. 57, No. 3, Advertising p. 31. Mar. 1969.
The Journal of Thoracic and Cardiovascular Surgery, G.J. Magovern, M.D. et al., vol. 59, No. 1, Jan. 1970, pp. 109–116.
The Bulletin of the Dow Corning Center for Aid to Medical Research, Silicone fluid as a lubricant for artificial eyes, vol. 6, No. 2, Apr. 1964, pp. 5–8.

*Primary Examiner*—David H. Willse

[57] ABSTRACT

There are disclosed various systems and methods for installing a synthetic, artificial heart valve within a patient. One system generally includes a plurality of sutures, each suture having a staple attached to a distal end thereof; a surgical stapler for radially discharging the staples into a heart at a location adjacent a site for installing the heart valve; a support assembly for releasably supporting the plurality of sutures; and a heart valve setter assembly, the heart valve setter assembly being operable to move the heart valve into position within the site in the heart. A method of installing a heart valve within a patient utilizing the system is provided and generally includes the steps of accessing a site within a heart from which a natural heart valve has been removed; positioning a surgical stapler within the site; discharging a plurality of staples, having sutures attached thereto, from the surgical stapler into the heart; lowering the heart valve along the sutures into position within the site in the heart; and securing the heart valve to the heart with the sutures.

17 Claims, 9 Drawing Sheets

U.S. PATENT DOCUMENTS

| | | |
|---|---|---|
| 3,587,115 | 6/1971 | Shiley . |
| 3,691,567 | 9/1972 | Cromie . |
| 3,722,004 | 3/1973 | Cromie . |
| 3,828,787 | 8/1974 | Anderson et al. . |
| 3,996,623 | 12/1976 | Kaster . |
| 4,056,854 | 11/1977 | Boretos et al. . |
| 4,233,690 | 11/1980 | Akins . |
| 4,506,394 | 3/1985 | Bédard . |
| 4,535,483 | 8/1985 | Klawitter et al. . |
| 4,585,453 | 4/1986 | Martin et al. . |
| 4,602,911 | 7/1986 | Ahmadi et al. . |
| 4,683,883 | 8/1987 | Martin . |
| 4,865,600 | 9/1989 | Carpentier et al. . |
| 4,932,965 | 6/1990 | Phillips . |
| 4,960,424 | 10/1990 | Grooters . |
| 5,041,130 | 8/1991 | Cosgrove et al. . |
| 5,074,858 | 12/1991 | Ramos Martinez . |
| 5,089,015 | 2/1992 | Ross . |
| 5,167,223 | 12/1992 | Koros et al. . |
| 5,197,979 | 3/1993 | Quintero et al. . |
| 5,236,450 | 8/1993 | Scott . |
| 5,290,300 | 3/1994 | Cosgrove et al. . |
| 5,326,373 | 7/1994 | Nagase . |
| 5,350,420 | 9/1994 | Cosgrove et al. . |
| 5,370,685 | 12/1994 | Stevens . |
| 5,403,305 | 4/1995 | Sauter et al. . |
| 5,423,851 | 6/1995 | Samuels . |
| 5,476,510 | 12/1995 | Eberhardt et al. . |
| 5,480,425 | 1/1996 | Ogilive . |
| 5,500,016 | 3/1996 | Fisher . |
| 5,509,930 | 4/1996 | Love . |
| 5,522,884 | 6/1996 | Wright . |
| 5,522,885 | 6/1996 | Love et al. . |
| 5,531,785 | 7/1996 | Love et al. . |
| 5,545,209 | 8/1996 | Roberts et al. . |
| 5,545,214 | 8/1996 | Stevens . |
| 5,571,170 | 11/1996 | Palmaz et al. . |
| 5,571,215 | 11/1996 | Sterman et al. . |
| 5,578,076 | 11/1996 | Krueger et al. . |
| 5,582,607 | 12/1996 | Lackman . |
| 5,584,879 | 12/1996 | Reimold et al. . |
| 5,593,435 | 1/1997 | Carpentier et al. . |
| 5,713,951 | 2/1998 | Garrison et al. . |
| 5,716,370 | 2/1998 | Williamson, IV et al. . |
| 5,716,398 | 2/1998 | Sparks et al. . |
| 5,716,401 | 2/1998 | Eberhardt et al. . |
| 5,716,402 | 2/1998 | Reif . |

FIG_2

STAPLING APPARATUS AND METHOD FOR HEART VALVE REPLACEMENT

BACKGROUND

1. Technical Field

The subject disclosure relates to minimally invasive surgical procedures and apparatus and, more particularly, to instruments and methods for performing heart valve replacement surgery.

2. Background of Related Art

The diagnosis and treatment of coronary disease and related conditions often requires repair or replacement of the valves located within the heart. Various factors, such as, for example, calcification, may result in the mitral or aortic valves becoming impaired or functionally inoperative requiring replacement. Where replacement of a heart valve is required, in general, the dysfunctional valve is cut out and replaced with either an artificial, synthetic heart valve or a harvested porcine heart valve. The replacement valve is typically sutured in place of the original valve.

Access to the heart in a patient's thoracic cavity is achieved by making a longitudinal incision in the chest. This procedure, referred to as a median sternotomy, includes cutting through the sternum and forcing the two opposing halves of the rib cage to be spread apart allowing access to the thoracic cavity and thus the heart.

Suitable instruments for spreading and holding apart the rib cage are marketed by United States Surgical Corporation, Norwalk, Conn. These instruments include, for example, Mini-CABG* retractors and related accessories. The Mini-CABG* universal retractor includes a substantially planar base having an opening which can be positioned on the patient such that the opening overlies the incision at the operative site. Mini-CABG* retractors are slidably mounted on the base and are provided to spread apart the rib cage halves and engage and retract obstructing tissue. The base may also be provided with surgical instruments which can be used to stabilize or manipulate the heart during surgery.

Once access to the thoracic cavity has been achieved, surgery on the heart to effect valve replacement may be performed. During some procedures, the heart beat is arrested by infusion of a cardioplegic fluid, such as potassium chloride (KCI), to paralyze the myocardium while blood flow circulation is maintained through known heart bypass techniques. Alternatively, the heart is allowed to beat to maintain circulation, while a localized area of the heart, on which surgery is to be performed, is locally immobilized by various instruments.

The heart is incised and the defective valve is cut away leaving a surrounding area of locally tougher tissue. Known heart valve replacement techniques typically include individually passing sutures through the tough tissue by hand to form an array of sutures. Free ends of the sutures are extended out of the thoracic cavity and laid, spaced apart, on the patient's body. The free ends of the sutures are then individually threaded through an edge around the circumference of the replacement valve or a supporting cuff. This is also typically accomplished by hand. Once all sutures have been run through the valve, all the sutures are pulled up taut and the valve is slid or "parachuted" down, by hand, into place adjacent the tough tissue. Thereafter, the replacement valve is secured in place using the sutures. Since the conventional heart valve replacement techniques are exclusively manual procedures, they are typically time consuming and difficult.

Where replacement is performed utilizing an artificial valve, hand held instruments in the form of a stick may be affixed to the valve and used to manipulate the replacement valve into place. The commercially available replacement valves are typically provided with a detachable holder structure which can be engaged by the hand tools.

While the above described procedures are sufficient to successfully position a heart valve within the heart, they are particularly time consuming. A more suitable apparatus would be desirable for maintaining the valve in a position such that a plurality of sutures may simultaneously pierce a cuff of the heart valve and thereafter assist in placement of the heart valve in the heart to allow it to be secured in place. Therefore, a need exists for apparatus and procedures of quickly and efficiently positioning and affixing artificial heart valves within the heart.

SUMMARY OF THE DISCLOSURE

There are provided various embodiments of systems and methods for installing a synthetic, artificial heart valve within a patient. The first system generally includes a plurality of sutures, each suture having a staple attached to a distal end thereof; a surgical stapler for radially discharging the staples into a heart at a location adjacent a site for installing the heart valve; a support assembly for releasably supporting the plurality of sutures; and a heart valve setter assembly, the heart valve setter assembly being operable to move the heart valve into position within the site in the heart.

Preferably the plurality of sutures also include a plurality of needles attached to a proximal end thereof. The needles may then be secured within a plurality of grooves on an inner surface of the support assembly with the pointed ends pointed proximally to facilitate insertion through a cuff of a replacement heart valve, and into a ring shaped needle guard mounted on the support assembly. The support assembly preferably includes a plurality of legs and a ring member, wherein the ring member is configured to interconnect the plurality of legs at a proximal end thereof.

The heart valve setter assembly, which includes a heart valve holder assembly and a heart valve setting instrument, may be mounted on the support assembly to lower the heart valve replacement into a predetermined location within the heart. The heart valve holder assembly includes a shaft, a handle connected to a proximal end of the shaft, and a heart valve holder connected to a distal end of the shaft. The heart valve setting instrument includes a shaft having a knurled proximal portion and a needle grasper connected to a distal end of the shaft, and is slidably mounted on the heart valve holder assembly. The heart valve is moved along the sutures into position within the predetermined site in the heart.

A method of installing a heart valve within a patient is provided and generally includes the steps of accessing a site within a heart from which a natural heart valve has been removed; positioning a surgical stapler within the site; discharging a plurality of staples, having sutures attached thereto, from the surgical stapler into the heart; lowering the heart valve along the sutures into position within the site in the heart; and securing the heart valve to the heart with the sutures.

The method of installing a heart valve within a patient, as described above, is preferably provided wherein the sutures have needles attached to an end opposite the staples. The method further includes the step of securing the sutures at a location above the site within the heart with a support assembly. Also, prior to the step of lowering the heart valve along the sutures, the sutures are threaded through a cuff of the heart valve to facilitate lowering the heart valve along the sutures into position within the site in the heart. Lastly, prior to the step of securing the heart valve to the heart, the heart valve installation assembly is removed from the accessed site.

BRIEF DESCRIPTION OF THE DRAWINGS

Various embodiments are described herein with reference to the drawings, wherein.

DETAILED DESCRIPTION OF PREFERRED EMBODIMENTS

Various embodiments are disclosed herein which relate to installation systems including tools and methods for quickly and efficiently positioning and securing a synthetic replacement heart valve within the heart without the necessity of manually suturing the valve in place. The disclosed systems accomplish this objective by providing a support assembly for supporting a plurality of sutures extending outward from a plurality of staples secured in a predetermined position within a site in a heart, and a setter assembly for guiding a replacement heart valve down along the suture lines into the predetermined position within the heart.

Figure 1:
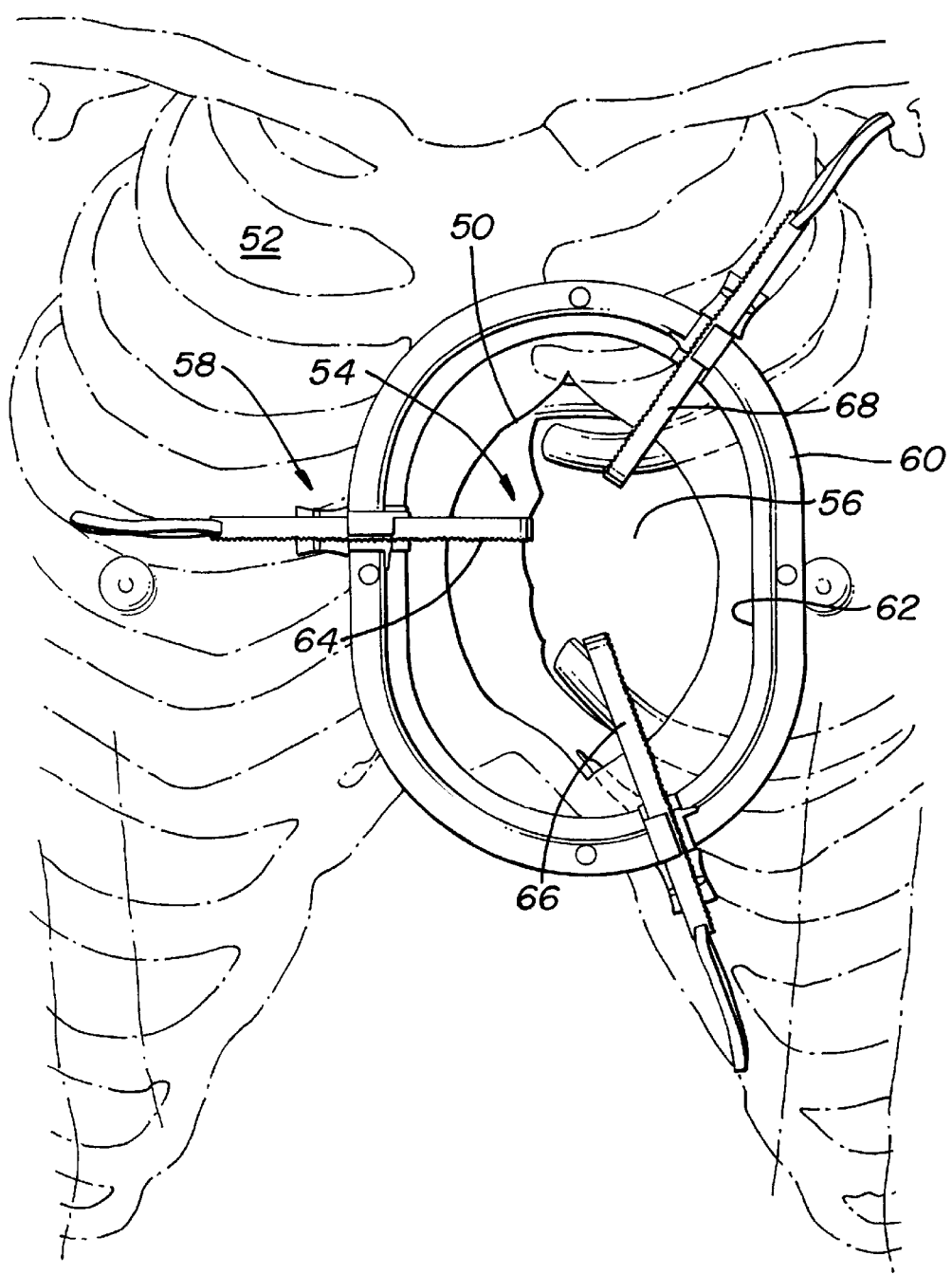
FIG. 1 is a perspective view of a patient with access to the thoracic cavity held open by a retractor.

Referring now to the drawings in detail, and initially to FIG. 1, access to the heart through the thoracic cavity is accomplished using well known surgical procedures. Generally, an incision 50 is made through the sternum of a patient 52 to access the thoracic cavity 54 and expose the heart 56.

Preferably, access to the cavity is maintained with the assistance of a retractor 58, such as, for example, the Mini-CABG* retractor and related accessories available from United States Surgical Corporation, Norwalk, Conn. Retractor 58 generally includes an oval planar base 60 and is positioned on patient 52 such that an opening 62 defined by base 60 overlies incision 50. A plurality of retractor blades 64, 66, 68 . . . are slidably mounted on base 60 and engage and retract the tissue edges of incision 50. Optionally, additional instruments may be affixed to base 60 to manipulate and/or stabilize the heart 56 to facilitate surgery thereon. Blood flow circulation may be maintained using known techniques. Thus, access to heart 56 is achieved and maintained. Other known open surgical procedures to access the heart are also contemplated and may be substituted for the procedure described herein. Once access to heart 56 has been obtained, heart 56 is opened and a dysfunctional valve is removed using known surgical procedures.

Figure 2:
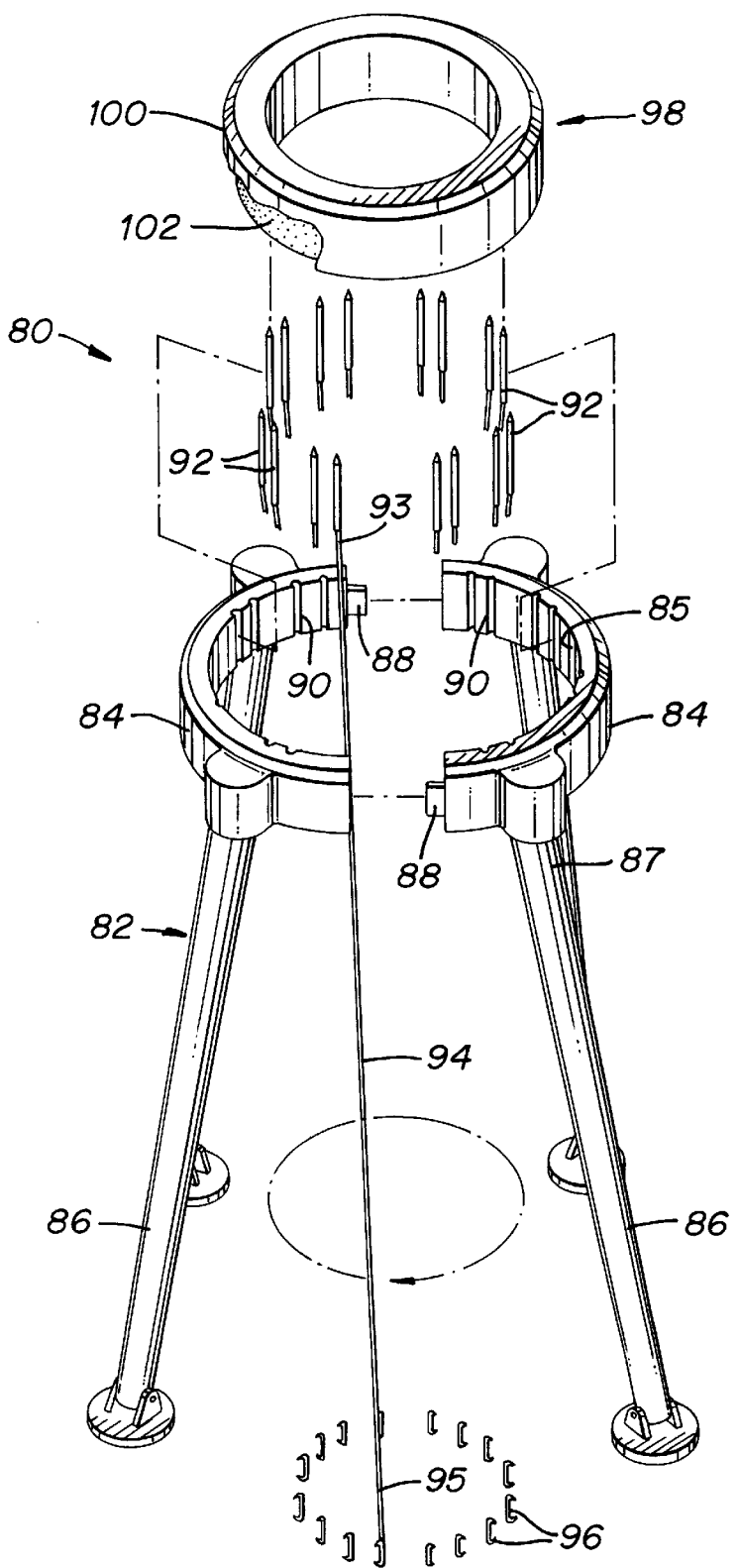
FIG. 2 is an exploded perspective view of a support assembly for use in heart valve replacement surgery.

Referring now to FIG. 2, there is disclosed a support assembly 80 for supporting and housing apparatus required for the replacement of a heart valve. Support assembly 80 includes a two-piece support member 82 which is preferably formed as a "quad-pod" which may be configured to be mounted on retractor base 60 shown in FIG. 1. Support member 82 includes a two-piece circular ring 84 and four legs 86. Ring 84 is attached to each of the four legs 86 at proximal ends 87 thereof. Each half of ring 84 contains a tab 88 extending therefrom on opposing sides thereof, the tabs 88 being configured and dimensioned to fit within an opening in the opposing ring half 84 to removably couple the two halves of ring 84. As used herein, the term "distal" refers to that portion of the assembly, or component thereof, further from the user, while the term "proximal" refers to that part of the assembly, or component thereof, closer to the user.

An inner surface 85 of ring 84 has a plurality of grooves or coaxial slots 90 formed therein for releasably securing a plurality of needles 92. As will be discussed in further detail below, needles 92 are preferably connected to proximal ends 93 of a plurality of sutures 94, and distal ends 95 of sutures 94 are connected to a corresponding plurality of staples 96.

Figure 3:
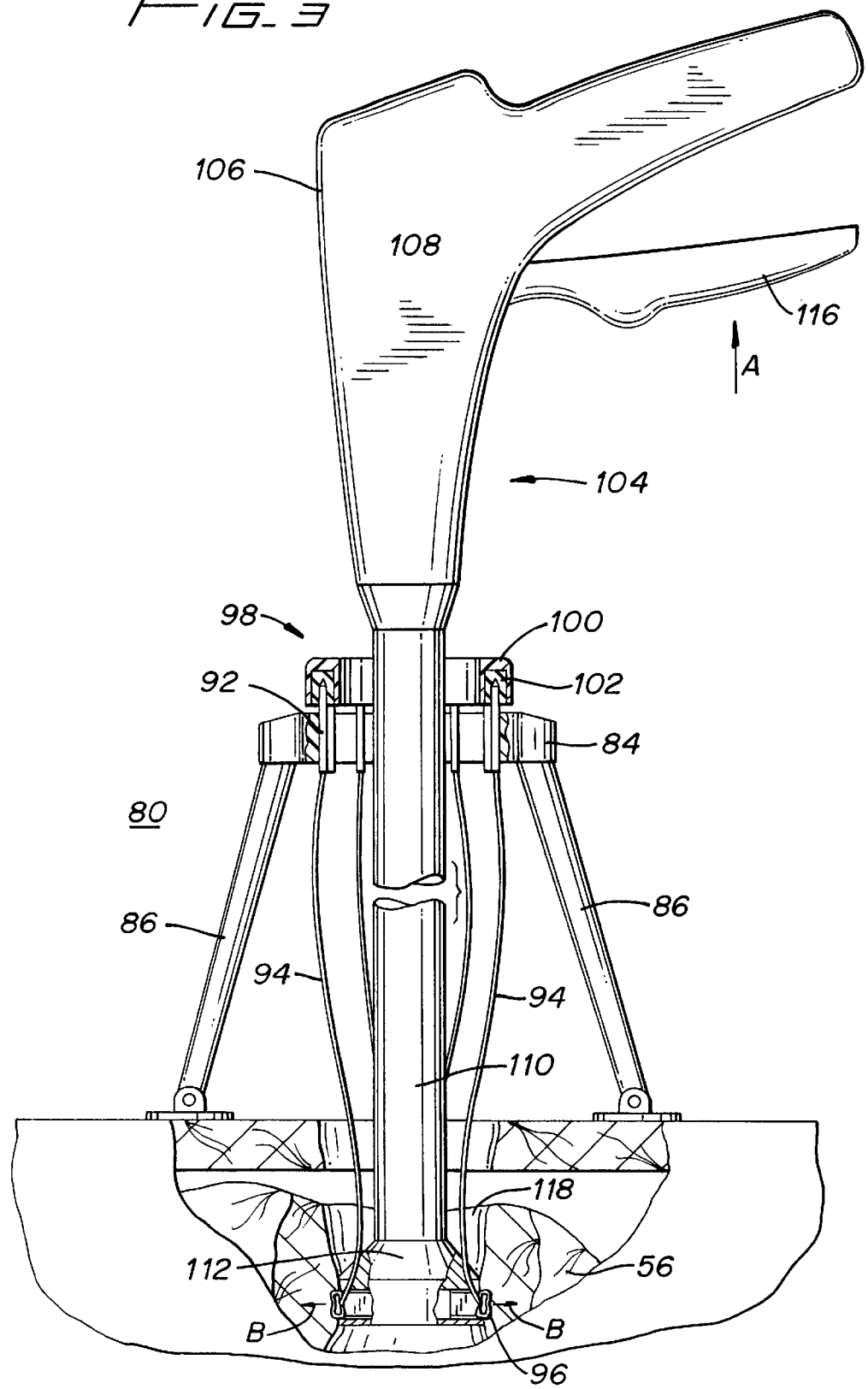
FIG. 3 is a partial cross-sectional side view of the support assembly of FIG. 2 having a surgical stapler positioned therein.

A needle guard 98 is removably mounted on a proximal surface of ring 84 and is positioned such that pointed ends of needles 92 pierce the lower surface of needle guard 98. As best seen in FIGS. 2 and 3, needle guard 98 preferably includes a plastic outer housing 100 having a circumferential groove therein, and a felt insert 102 positioned within the circumferential groove for releasably retaining the plurality of needles 92.

Referring now to FIG. 3, to install an artificial heart valve in heart 56, support assembly 80 is positioned above an opening to a thoracic cavity of a patient and a surgical stapler 104 is positioned therein. A proximal end 106 of stapler 104 includes an actuator handle 108 which is operatively connected through shaft 110 to a staple retainer housing 112 located on a distal end 114 of stapler 104.

A plurality of staples 96, which are preassembled with sutures 94 and needles 92, are loaded into staple retainer housing 112 prior to being discharged into the intended surrounding tissue. Actuator handle 108 is configured such that a lever 116 is moved in the direction of arrow A to cause one or more staples to be simultaneously discharged from staple retainer housing 112 in a radial direction as indicated by arrows B illustrated adjacent staple retainer housing 112. Preferably, stapler 104 is configured to discharge a plurality of staples 96 in a single shot i.e., a single actuation of lever 116. Alternatively, stapler 104 may be configured to hold and discharge a single staple 96 in response to an actuation of lever 116. Thus, stapler 104 is a means for attaching a distal end of sutures to a heart.

As illustrated in FIG. 3, distal end 114 of stapler 104 is positioned within a bore 118 in heart 56 which was created by the removal of a dysfunctional heart valve. Typically, following removal of a dysfunctional heart valve, the surrounding area includes tougher tissue which is amenable to retaining staples and sutures. Once lever 116 is depressed, staples 96 are discharged into the circumference of bore 118 formed in heart 56, and stapler 104 may be removed from support assembly 80. Following removal of stapler 104, support assembly 80 may remain positioned above the thoracic cavity of a patient and ready to receive additional tools. Sutures 94 extend proximally from staples 96, which are secured to heart 56, and are attached to needles 92 which are removably secured within ring 84 and needle guard 98.

Alternatively, it is contemplated that the distal ends of sutures 94 may be manually attached to heart 56 (e.g., by threading), instead of using staples 96.

At this point, needle guard 98 may be removed to expose the pointed ends of needles 92. A heart valve may then be manually positioned adjacent needles 92 such that needles 92 are caused to penetrate a cuff of the heart valve. The needles may then be pulled through the cuff with a conventional needle grasper to allow the heart valve to slide down the sutures into position within the heart. However, it is preferable to use a heart valve setter assembly in accordance with the present disclosure and discussed below.

Figure 4:
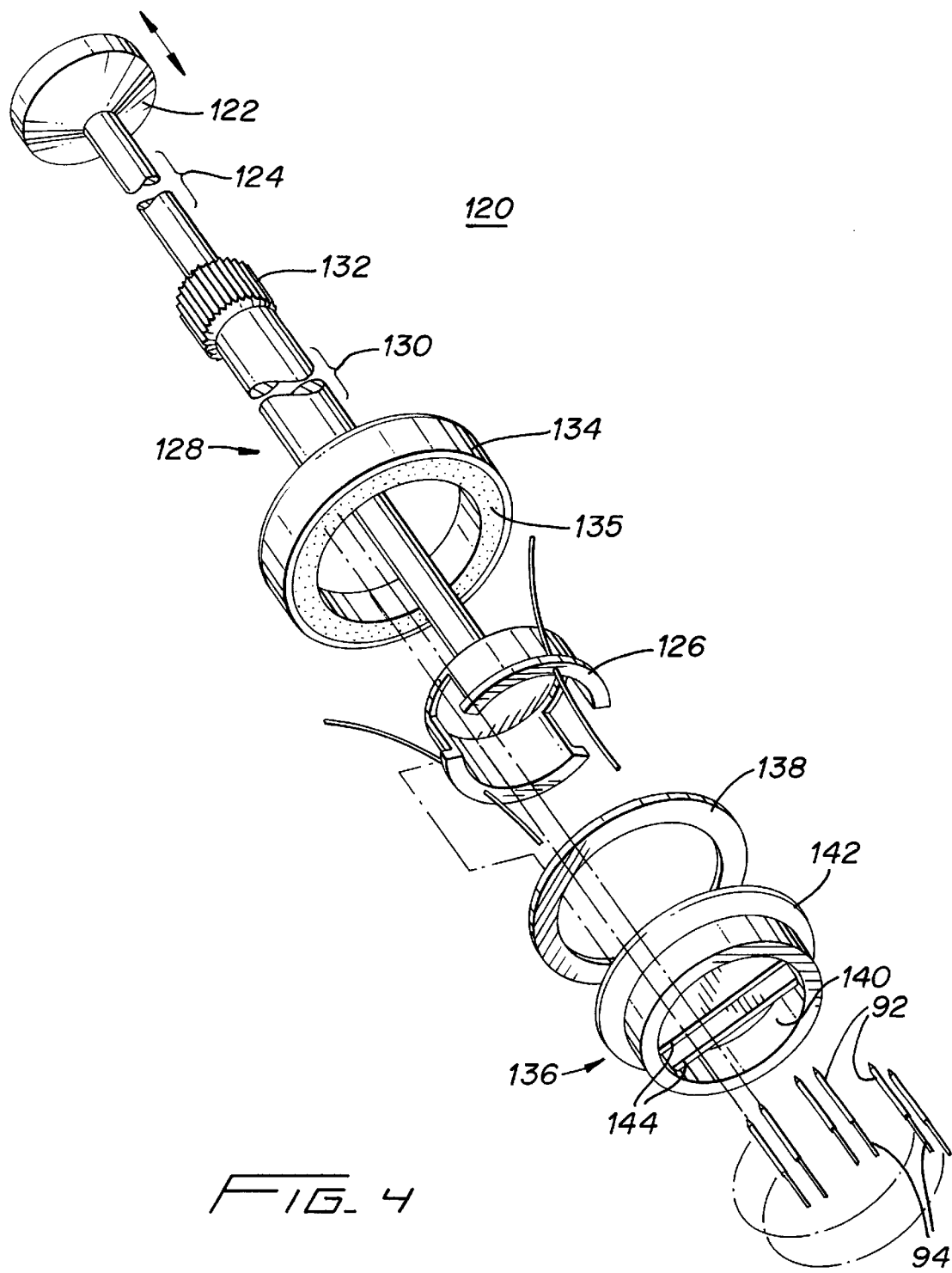
FIG. 4 is an exploded perspective view of a heart valve setter assembly.

Referring now to FIG. 4, there is disclosed a heart valve setter assembly 120 for use with support assembly 80 during heart valve replacement surgery. Heart valve setter assembly 120 includes a heart valve holder assembly having a handle 122 connected to a proximal end of a shaft 124, a heart valve holder 126 connected to a distal end of shaft 124 and a valve setting instrument 128 having a longitudinal bore therein for slidably mounting on shaft 124. Valve setting instrument 128 includes a shaft 130 having a knurled proximal portion 132 and a needle grasper 134 connected to a distal end. Similar to needle guard 98, needle grasper 134 has a permeable felt insert 135 therein.

Also illustrated in FIG. 4 are heart valve assembly 136, suture retainer ring 138 and needles 92 which are attached to sutures 94. Heart valve assembly 136 includes a valve cuff 142 and a valve ring 140 having a plurality of valve leaflets 144 pivotally mounted therein. Heart valve ring 140 is generally formed by molding or machining a suitable biocompatible material such as, for example, stainless steel. Valve cuff 142 is preferably formed of a permeable felt, to facilitate penetration thereof by needles 92.

Figure 5:
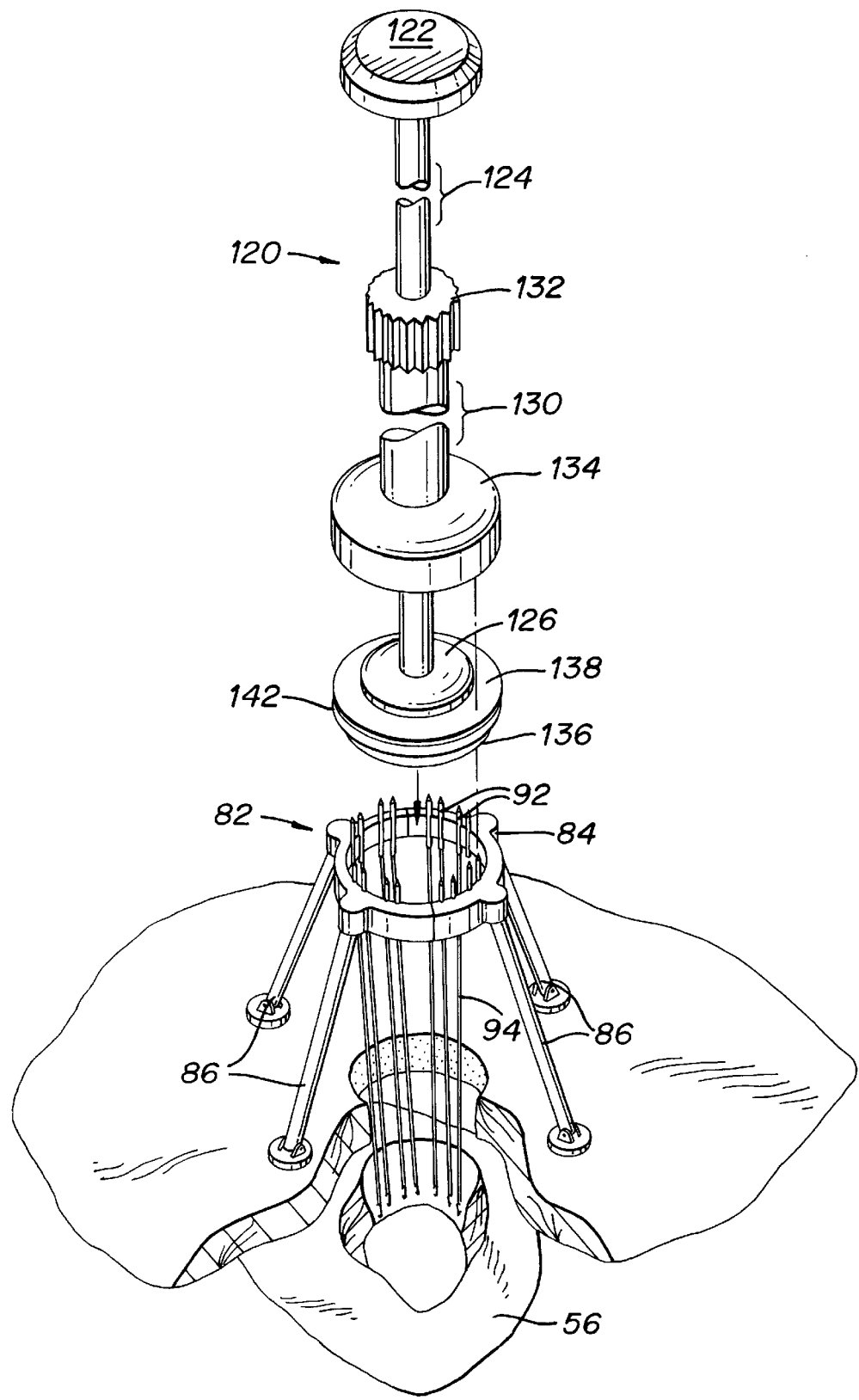
FIG. 5 is an exploded perspective view of the heart valve setter assembly of FIG. 4 being installed on the support assembly of FIG. 2.

Referring to FIG. 5, to proceed with the operation, needle guard 98 (FIG. 3) has been removed to facilitate exposure of the pointed ends of needles 92 secured within ring 84. Heart valve assembly 136 and suture retainer ring 138 are held by valve holder 126. The entire heart valve setter assembly 120 is then moved distally in the direction of support member 82 such that needles 92 penetrate valve cuff 142 and suture retainer ring 138, and heart valve setter assembly 120 is mounted on support member 82.

Figure 6:
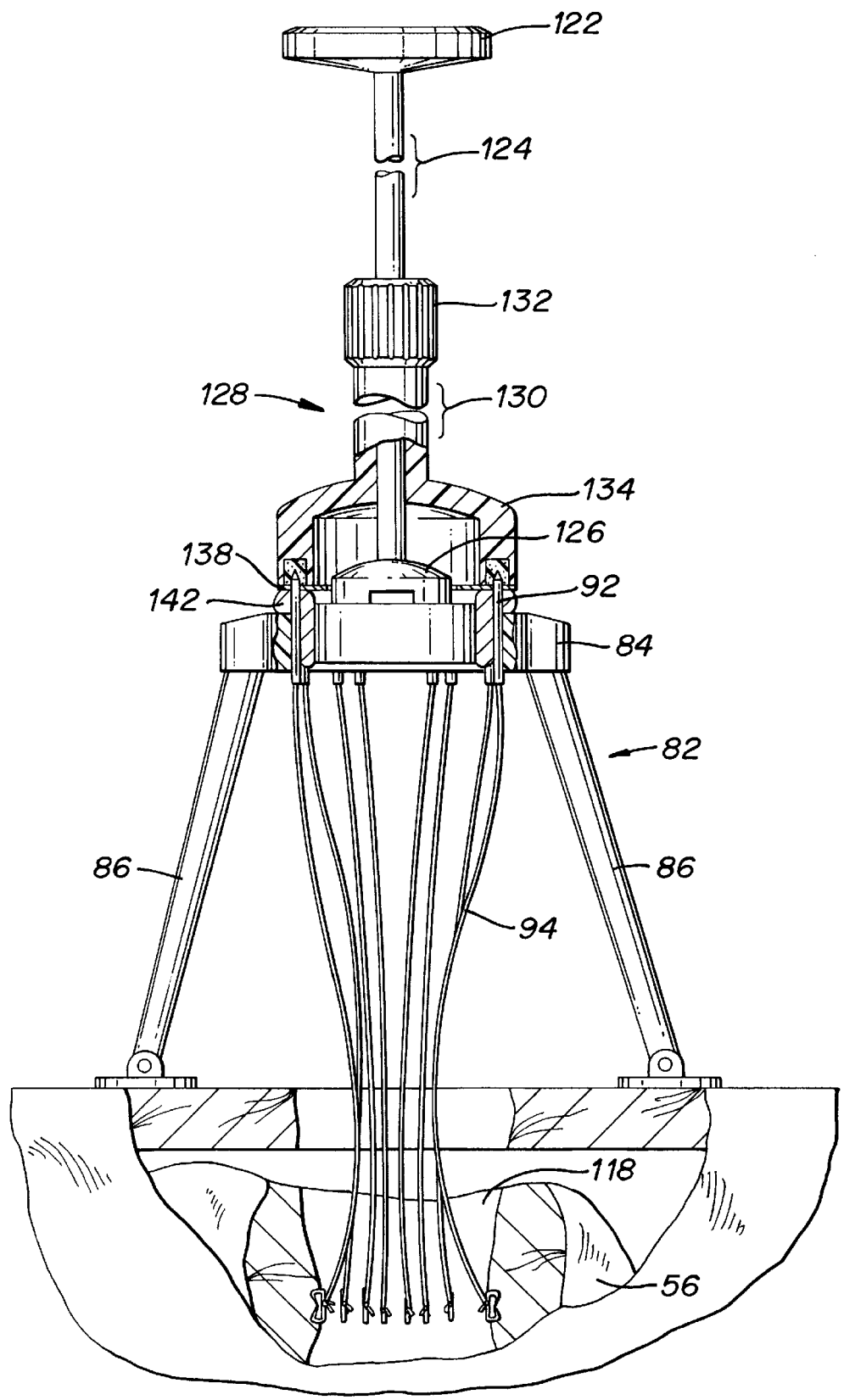
FIG. 6 is a view of the heart valve setter assembly mounted on the support assembly above an opening in a thoracic cavity.

Turning now to FIG. 6, heart valve setter assembly 120 is shown mounted on support member 82, as described above, with needles 92 penetrating through valve cuff 142 and suture retainer ring 138. As illustrated, valve setting instrument 128 has been shifted distally along shaft 124 such that needles 92 are secured within needle grasper 134. Specifically, needles 92 penetrate cuff 142 and engage permeable felt insert 135 within needle grasper 134. Heart valve assembly 136 is now ready to be parachuted distally along sutures 94 and into its intended position within bore 118 of heart 56.

Figure 7:
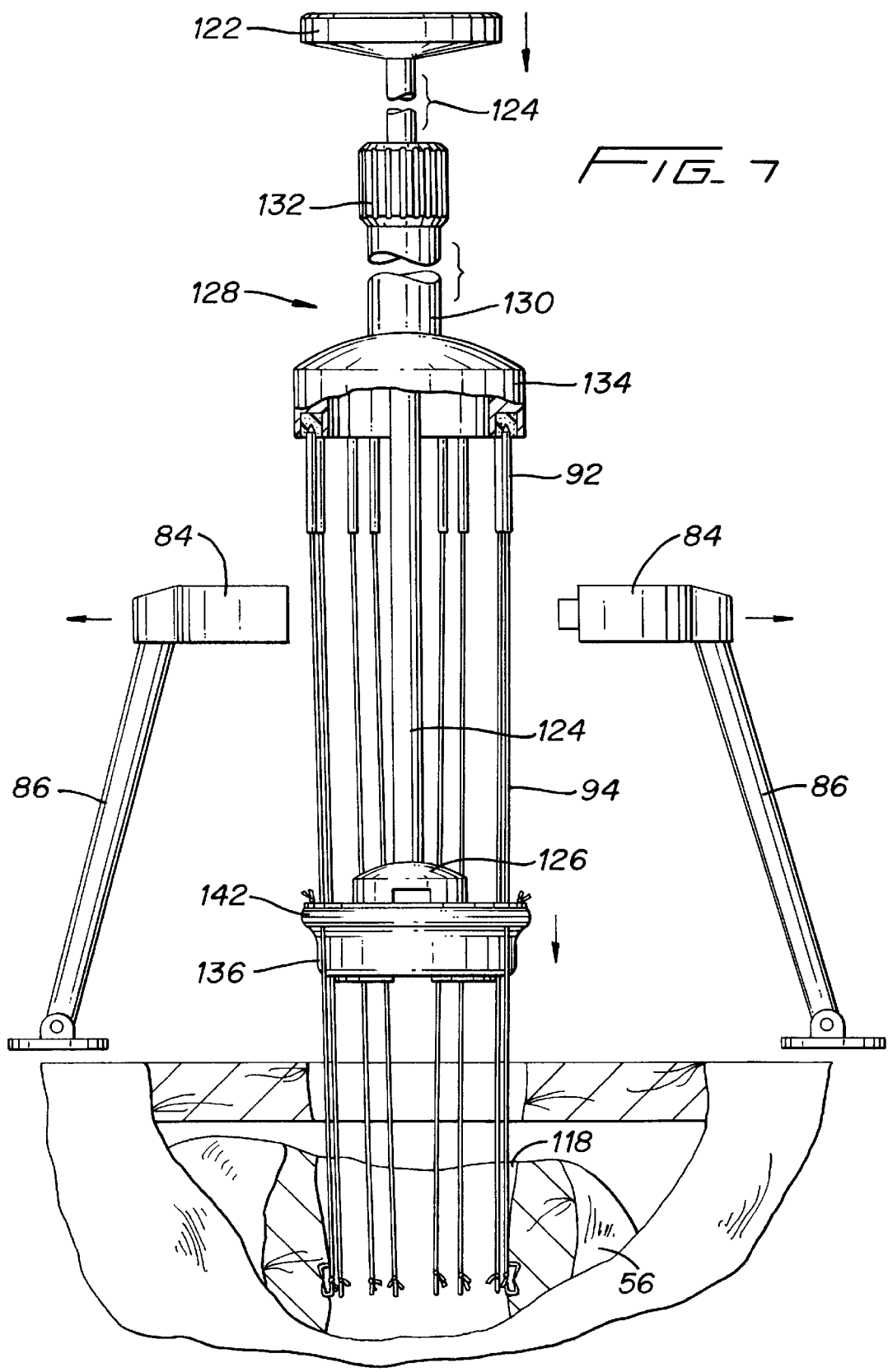
FIG. 7 is a view of the support assembly being separated to allow a heart valve to parachute down into a bore in a heart.

Turning now to FIG. 7, the two halves of support member 82 are separated and moved outward from heart valve assembly 136 releasing needles 92 from coaxial slots 90 to allow assembly 136 to be moved or parachuted distally along sutures 94 into bore 118 of heart 56. To initiate and control the distal movement of heart valve assembly 136, valve setting instrument 128 is secured in a fixed position relative to handle 122, shaft 124 and heart valve holder 126. While knurled portion 132 is held, handle 122 may be depressed to force heart valve holder 126 to push heart valve assembly 136 distally, thereby freeing it from being held adjacent needle grasper 134 by needles 92 within valve cuff 142. Heart valve assembly 136 may be guided distally along the sutures lines 94 by heart valve holder 126. The velocity of the distal movement of heart valve assembly 136 may be controlled by the user via handle 122.

Figure 8:
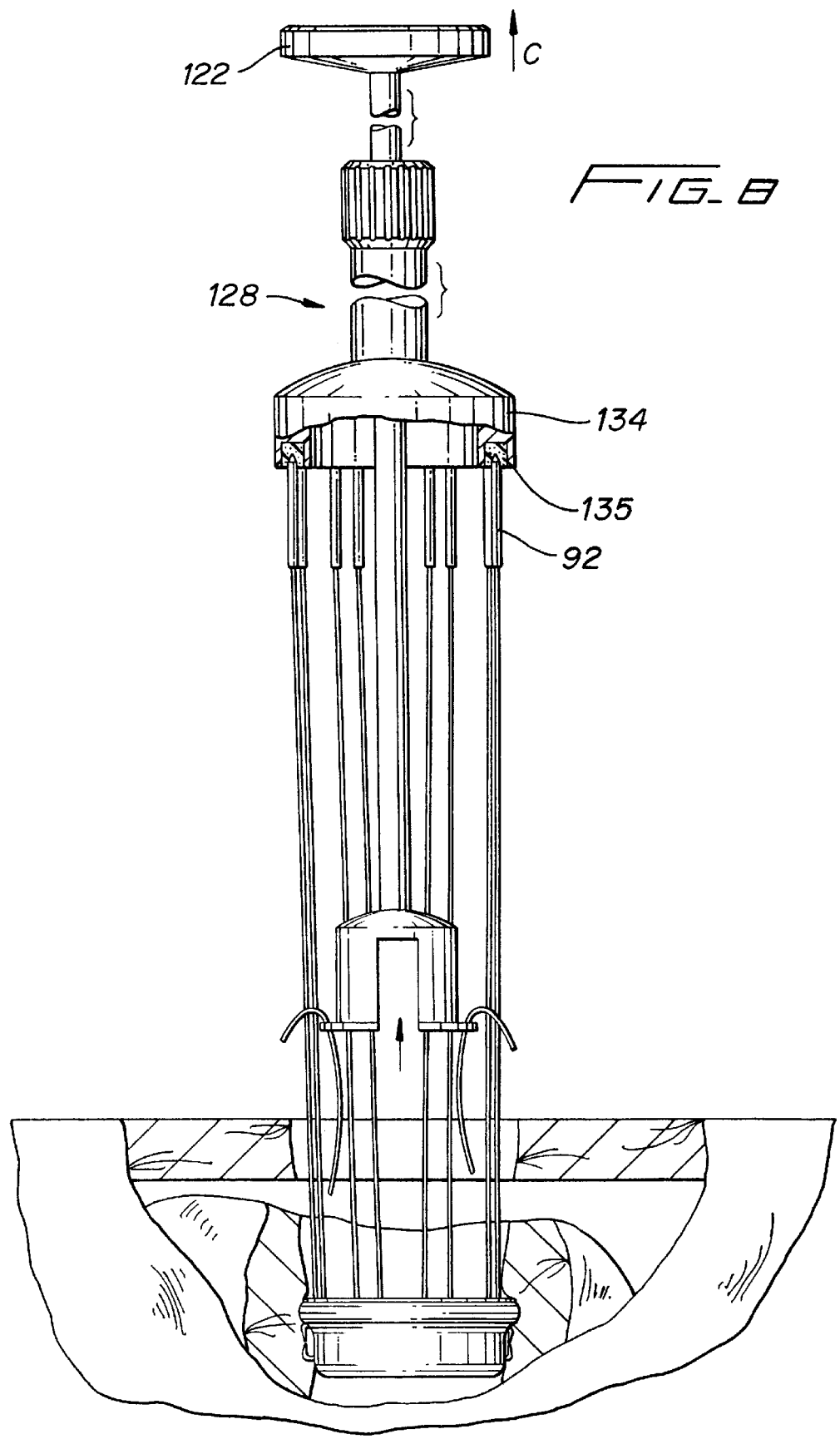
FIG. 8 is a view illustrating the removal of a heart valve holder from the heart valve.

Once heart valve assembly 136 is properly positioned adjacent staples 96 within bore 118 of heart 56, handle 122 is drawn proximally, as indicated by arrow C, to remove heart valve holder 126 from heart valve assembly 136, as shown in FIG. 8. Thereafter, valve setting instrument 128 may be moved proximally to release needles 92 from permeable felt 135 within needle grasper 134. Alternatively, sutures 94 may be cut at the proximal end thereof, leaving pointed needles 92 engaged with permeable felt 135 within needle grasper 134.

Figure 9:
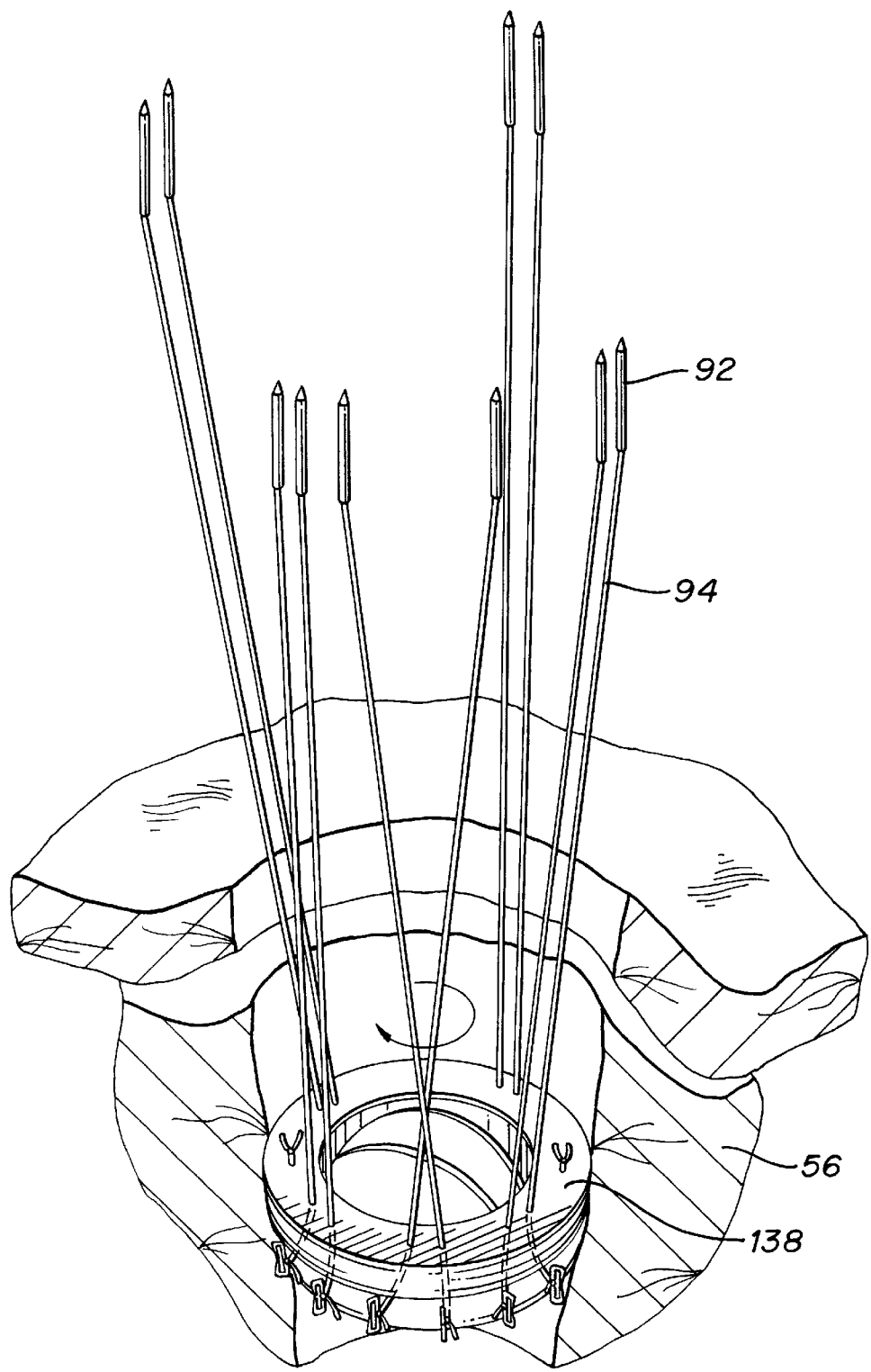
FIG. 9 is a perspective view of a plurality of sutures extending upward from a heart valve positioned within a bore of a heart.

As illustrated in FIG. 9, valve setting instrument 128 has been removed leaving heart valve assembly 136 and suture retainer ring 138 positioned within bore 118 of heart 56 with sutures 94 and needles 92 extending therethrough. To complete the installation of heart valve assembly 136, adjacent pairs of sutures 136 may be tied and cut adjacent suture retainer ring 138, or secured adjacent suture retainer ring 138 by any other suitable means known to one having ordinary skill in the art.

It will be understood that various modifications may be made to the embodiments disclosed herein. For example, it is noted that variously dimensioned heart valve assemblies may be provided to facilitate replacement of corresponding heart valves. Therefore, the above description should not be construed as limiting but merely as exemplifications of preferred embodiments. Those skilled in the art will envision other modifications within the scope and spirit of the claims appended hereto.

What is claimed is:

1. A system for installing a heart valve within a patient comprising:
   a plurality of sutures, each suture having a staple attached to a distal end thereof;
   a surgical stapler for discharging the staples into a heart at a location adjacent a site for installing the heart valve;
   a support assembly for releasably supporting the plurality of sutures; and
   a heart valve setter assembly, the heart valve setter assembly being operable to engage the plurality of sutures with the heart valve and move the heart valve into position within the site in the heart.

2. The system of claim 1, further comprising a plurality of needles attached to proximal ends of the plurality of sutures.

3. The system of claim 1, wherein the surgical stapler discharges at least one staple in a radial direction to engage the heart at a predetermined location.

4. The system of claim 1, wherein the heart valve is moved along the sutures into position within the site in the heart.

5. The system of claim 2, wherein the support assembly includes a plurality of legs and a ring member, the ring member configured to interconnect the plurality of legs at a proximal end thereof.

6. The system of claim 5, wherein the ring member includes a plurality of grooves on an inner surface thereof for releasably securing the plurality of needles.

7. The system of claim 6, wherein the support assembly further includes a ring shaped needle guard mounted on the ring member.

8. The system of claim 1, wherein the heart valve setter assembly comprises a heart valve holder assembly and a heart valve setting instrument.

9. The system of claim 8, wherein the heart valve holder assembly includes a shaft, a handle connected to a proximal end of the shaft, and a heart valve holder connected to a distal end of the shaft.

10. The system of claim 8, wherein the heart valve setting instrument includes a shaft having a knurled proximal portion and a needle grasper connected to a distal end of the shaft.

11. The system of claim 8, wherein the heart valve setting instrument is slidably mounted on the heart valve holder assembly.

12. A system for installing a heart valve within a heart comprising:

a plurality of sutures;

means for attaching a distal end of the plurality of sutures to the heart at a location adjacent a site for installing the heart valve;

a support assembly for releasably supporting the plurality of sutures;

a heart valve setter assembly, the heart valve setter assembly being operable to engage the plurality of sutures with the heart valve and move the heart valve into position within the site in the heart; and a plurality of needles attached to proximal ends of the plurality of sutures;

wherein the support assembly includes a plurality of legs, a ring member and a ring shaped needle guard mounted on the ring member, the ring member including a plurality of grooves on an inner surface thereof for releasably securing plurality of needles and configured to interconnect the plurality of legs at a proximal end thereof.

13. The system of claim 12, wherein the heart valve is moved along the sutures into position within the site in the heart.

14. The system of claim 12, wherein the heart valve setter assembly comprises a heart valve holder assembly and a heart valve setting instrument.

15. The system of claim 14, wherein the heart valve holder assembly includes a shaft, a handle connected to a proximal end of the shaft, and a heart valve holder connected to a distal end of the shaft.

16. The system of claim 14, wherein the heart valve setting instrument includes a shaft having a knurled proximal portion and a needle grasper connected to a distal end of the shaft.

17. The system of claim 14, wherein the heart valve setting instrument is slidably mounted on the heart valve holder assembly.

* * * * *